United States Patent
Dury

(10) Patent No.: US 6,191,309 B1
(45) Date of Patent: Feb. 20, 2001

(54) METHOD FOR PREPARING HALOGENATED 2-AMINO OR 2-ACETAMIDO TRIFLUOROMETHYLBENZENE DERIVATIVES

(75) Inventor: Michel Dury, Lyons (FR)

(73) Assignee: Rhodia Chimie, Courbevoie Cedex (FR)

( * ) Notice: Under 35 U.S.C. 154(b), the term of this patent shall be extended for 0 days.

(21) Appl. No.: 09/230,044

(22) PCT Filed: Jul. 16, 1997

(86) PCT No.: PCT/FR97/01323

§ 371 Date: Mar. 2, 1999

§ 102(e) Date: Mar. 2, 1999

(87) PCT Pub. No.: WO98/02409

PCT Pub. Date: Jan. 22, 1998

(30) Foreign Application Priority Data

Jul. 16, 1996 (FR) .................................... 96 08885

(51) Int. Cl.⁷ .................... C07C 233/05; C07C 209/74
(52) U.S. Cl. ................. 564/218; 564/412; 564/442
(58) Field of Search ...................... 564/412, 442, 564/218

(56) References Cited

U.S. PATENT DOCUMENTS 2,093,115  9/1937  Wolfram et al. .
4,008,278  2/1977  Boudakian .

FOREIGN PATENT DOCUMENTS 800 343  7/1936  (FR) .

OTHER PUBLICATIONS

Finar, I. L., Organic Chemistry, vol. 1, Chapter XXIV, pp. 583–584, 1964.*

Patent Abstracts of Japan, vol. 012, No. 306 (C–552), Aug. 19, 1988 & JP 63 077844 A (Nippon Kayaku, Co. Ltd.) Apr. 8, 1988, see abstract.

Patent Abstracts of Japan, vol. 006, No. 085 (C–103), May 22, 1982 & JP 57 018638 A (Sagami Chem Res Center), Jan. 30, 1982, cited in the application, see abstract.

* cited by examiner

*Primary Examiner*—Shailendra Kumar
(74) *Attorney, Agent, or Firm*—Burns, Doane, Swecker & Mathis, L.L.P.

(57) ABSTRACT

The halogenation of a compound of formula (1) or formula (2'), wherein Q is an $NH_2$ group optionally in the form of an addition salt, or an $NHCOCH_3$ group, and X is a halogen atom, using a compound of formula $X_2$, in a solvent selected from an anhydrous halogenated hydrocarbon, a mixture of water and a halogenated hydrocarbon and optionally the compound of formula (1) itself, gives a 2-amino or 2-acetamido trifluoromethylbenzene halogenated in the 5 position of the benzene ring.

(1)

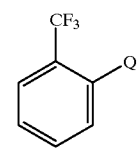

(2')

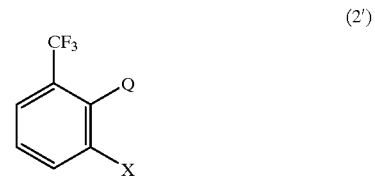

18 Claims, No Drawings

METHOD FOR PREPARING HALOGENATED 2-AMINO OR 2-ACETAMIDO TRIFLUOROMETHYLBENZENE DERIVATIVES

This application is a 371 of PCT/FR97/01323, filed Jul. 16, 1997.

The present invention relates to a process for preparing 2-amino- or 2-acetamidotrifluoromethylbenzene derivatives halogenated in position 5 on the benzene ring.

5-Chloro-2-aminotrifluoromethylbenzene is a synthetic intermediate which is used in particular in the manufacture of dyes, or of a fungicide, triflumizole.

Many synthetic routes have been proposed to reach this compound, usually in at least two steps starting from a simple precursor.

Thus, patent FR-A-800,343 describes the preparation of 5-chloro-2-aminotrifluoromethylbenzene from 3-chlorotrifluoromethylbenzene by nitration in a nitric acid/sulphuric acid mixture, followed by a reduction.

More recently, one-step processes have been proposed. Patent JP-A-57,018,638, dated Jul. 7, 1980 describes the trifluoromethylation of p-chloroaniline.

Chlorination of 2-aminotrifluoromethylbenzene has also been envisaged, but it is difficult to obtain the desired chlorination product with sufficient selectivity.

Patent U.S. Pat. No. 4,008,278 presents a solution for avoiding the formation of monochlorination products other than 5-chloro-2-aminotrifluoromethylbenzene. This consists in reacting 2-aminotrifluoromethylbenzene, or an N-acetyl or N-formyl derivative, with hydrochloric acid in the presence of an oxidant.

The starting reagent is converted into 5-chloro-2-aminotrifluoromethylbenzene to 64.5%, to 3,5-dichloro-2-aminotrifluoromethylbenzene to 34.2% and only traces of 3-chloro-2-aminotrifluorobenzene are detected.

However, the selectivity of the reaction under these conditions remains insufficient since the mono- and dichlorination products are obtained in a ratio of about 2:1. This imposes a final step of separation of the isomers, in which a large volume of reaction product needs to be treated in order to isolate the desired compound. The production efficiency of such processes is thus poor.

The aim of the invention is to propose operating conditions which impose high selectivity on the halogenation reaction of 2-amino- or 2-acetamidotrifluoromethylbenzene for improved production efficiency.

Other aspects of the invention relating to this objective will become apparent later.

It turns out that improved selectivity can be achieved by carrying out the halogenation under the action of a dihalogen gas in a specific solvent.

Thus, the subject of the invention is a process for preparing 2-amino- or 2-acetamidotrifluoromethylbenzene which is halogenated in position 5, comprising a step of halogenating a compound of formula (1)

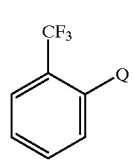

(1)

in which Q represents an $NH_2$ group optionally in the form of an addition salt with an acid such as hydrochloric acid, or an $NHCOCH_3$ group, by using a compound of formula $X_2$ where X represents a halogen atom, in a solvent chosen from an anhydrous halogenated hydrocarbon, a mixture of water and of halogenated hydrocarbon and the compound of formula (1) itself, to give mainly a compound of formula (2) or (3)

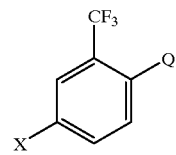

(2)

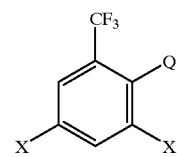

(3)

in which formulae Q and X are as defined above.

The starting material of formula (1) can be 2-aminotrifluoromethylbenzene (Q=$NH_2$), in which the amino group is optionally in the form of an addition salt with an acid which is known per se, in particular such as hydrochloric acid, or alternatively, 2-acetamidotrifluoromethylbenzene (Q=$NHCOCH_3$).

These compounds have more or less identical reactivity with respect to halogenation under the conditions of the invention.

The halogenation reaction according to the present invention does not require the presence of an organic base.

The halogen atom(s) which can be grafted onto the benzene ring according to the invention comprise iodine, bromine and chlorine, with a preference for bromine and chlorine, most particularly for chlorine.

The halogenation reagent will be chosen, as a function of the desired halo derivative, from $Cl_2$, $Br_2$ and $I_2$.

It is seen that the choice of solvent makes it possible to direct the regioselectivity for the introduction of the halogen atom(s).

Thus, when the reaction is carried out in an anhydrous halogenated hydrocarbon, the product of formula (2) is mainly obtained. The isomer monochlorinated in position 3 is present at the end of the reaction only in trace amounts.

In point of fact, it has been demonstrated that this compound can be formed during the reaction but is totally converted into dihalo compound of formula (3) as the reaction proceeds. The compound of formula (3) is formed in only limited amounts, and the yields of compounds (2) and (3) are in a (2)/(3) molar ratio of at least 3:1.

In order to guarantee maximum selectivity and to avoid the presence of isomer monohalogenated in position 3, it is preferable to carry out the process until complete or virtually complete conversion. Advantageously, the halogenation reaction is carried out until the degree of conversion of the compound of formula (1) is at least 80%, preferably at least 85% and even at least 90% (the degree of conversion DC being the molar ratio of the amount of compound (1) consumed during the reaction to the initial amount of compound (1).

The yield for conversion of the compound of formula (1) into compound of formula (2) which is generally achieved is about 70% or more, advantageously at least 75% and even at least 80% (the yield for conversion CY of (1) into (2)

being the molar ratio of the amount of compound (2) formed to the amount of compound (1) consumed).

As regards the appropriate halogenated hydrocarbons, these can be either aliphatic or aromatic hydrocarbons. Mention may be made in particular of dichloromethane, monochlorobenzene, dichlorobenzene or trifluoromethylbenzene.

Advantageously, the reagent $X_2$ is introduced gradually into the reaction solvent during the reaction, optionally portionwise, preferably continuously.

Advantageously, the amount of $X_2$ introduced into the reaction medium is such that the molar ratio of the amount of $X_2$ introduced to the amount of compound of formula (1) is from 1 to 2 approximately.

The compound of formula (1) can be introduced in a single portion into the reaction mixture at the start of the reaction, or it can be introduced gradually, in the same way as the halogenation reagent, during the reaction.

According to one variant of the invention, it is possible to carry out the halogenation reaction without solvent or, more exactly, in a solvent consisting of the compound of formula (1) itself.

Under these conditions, the compound of formula (2) is also mainly formed, with a yield for conversion of (1) into (2) of about 70% or more, in particular of at least 75%, advantageously of at least 80%.

In order for some of the compound of formula (1) to be able to act as solvent, this compound must be in relative excess relative to the halogenation reagent introduced. Advantageously, the molar ratio of the amount of $X_2$ introduced to the initial amount of compound of formula (1) is from about 0.1 to about 0.5.

The degree of conversion of the compound of formula (1) will be proportionately more limited the greater the excess of this compound. In contrast with the preceding variant, on account of the incomplete conversion, a mixture of isomers monohalogenated mainly in position 5 and to a minor extent in position 3 is obtained.

However, on account of the larger amount of compound (1) capable of reacting in a given volume of reactor and on account of the very high conversion yield (selectivity) in favour of the 5-halo isomer, the production efficiency of this isomer is excellent, being about 300 kg/m³ of reaction mixture. Under these conditions, the separation of the isomers by distillation does not place an excessive burden on the production cost and the overall production efficiency is thus satisfactory.

According to a third variant, the selectivity can be totally reversed in favour of the dihalo compound of formula (3) by choosing a solvent consisting of a mixture of water and a halogenated hydrocarbon, such as those described above, and by introducing the compound of formula (1), along with the reagent $X_2$, gradually, advantageously continuously, into the reaction solvent.

Preferably, the solvent contains at least 20%, for example from 20 to 80%, by weight of halogenated hydrocarbon, advantageously at least 30%, in particular about 50% by weight.

In order to achieve the dihalogenation, the amount of $X_2$ introduced is advantageously from about 1.5 to about 2.5 mol per mole of compound of formula (1).

The yield for conversion into the compound of formula (3) is at least 70%, advantageously 75% or more.

The halogenation reaction in these three variants advantageously takes place at a temperature of about from 5 to 80° C. Preferably, when the starting compound of formula (1) is 2-amino-trifluoromethylbenzene or an addition salt derived therefrom, the temperature of the reaction medium is from 5 to 50° C., advantageously from 5 to 20–25° C., and when the starting compound of formula (1) is 2-acetamidotrifluoromethylbenzene, the temperature of the reaction medium is from 70 to 80° C.

As stated previously, the present invention provides means for carrying out the complete or virtually complete halogenation reaction of a 2-amino- or 2-acetamidotrifluoromethylbenzene derivative halogenated in position 3 to give the dihalo derivatives of formula (3).

In this regard, the invention also relates to a process for preparing a dihalo derivative of 2-amino- or 2-acetamidotrifluoromethylbenzene, comprising a step of halogenating a compound of formula (2')

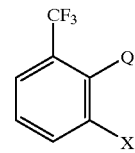

(2')

in which Q represents an $NH_2$ group optionally in the form of an addition salt with an acid such as hydrochloric acid, or an $NHCOCH_3$ group, and X represents a halogen atom, by using a compound of formula $X_2$ in a solvent containing a halogenated hydrocarbon.

The conversion of the compound (2') into the compound of formula (3) can be obtained completely in a mixture of halogenated hydrocarbon and water, but also in an anhydrous halogenated hydrocarbon, provided that care is taken to ensure that the degree of progress is high.

This reaction makes it possible to upgrade compounds of formula (2') which are by-products of the halogenation reaction and which are of no intrinsic use.

When the compound of formula (1) is 2-acetamidotrifluoromethylbenzene, the group $Q=NHCOCH_3$ remains intact during the halogenation reaction. It can, if so desired, be converted into an amino group by solvolysis in a suitable solvent, such as an alcohol. A methanolysis with refluxing methanol or a hydrolysis will be carried out, for example.

Thus, a subject of the invention is also a process for preparing halo-2-aminotrifluoromethylbenzene, comprising a step of halogenating 2-acetamido-trifluoromethylbenzene

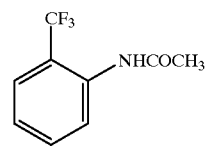

by using a compound of formula $X_2$ where X represents a halogen atom, in accordance with a process described above to form the 5-halo-2-acetamidotrifluoromethylbenzene of formula (2)

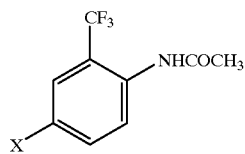

followed by a step of solvolysis of the compound of formula (2) obtained.

The selective mono- or dihalogenation process according to the invention can be exploited in a reaction sequence by ensuring that this sequence has a high overall yield of the desired product.

Thus, another subject of the invention is a process for preparing 3,5-dichlorotrifluoromethylbenzene, comprising a step of dihalogenating 2-amino-trifluoromethylbenzene using a compound of formula $X_2$ where X represents a halogen atom, the reagents being introduced simultaneously and gradually into a solvent consisting of a mixture of halogenated hydrocarbon and water, followed by a step of diazotization-reduction of the 2-amino-3,5-dihalotrifluoromethylbenzene obtained (formula (3)), in the presence of hypophosphorous acid $HPO_2$ and sodium nitrite $NaNO_2$.

The diazotization-reduction reagent $HPO_2/NaNO_2$ can be used in a manner which is known per se.

Preferably, the reaction temperature in this step is less than or equal to 30° C.

The examples which follow illustrate the invention in greater detail.

EXAMPLE 1

Chlorination of 2-aminotrifluoromethylbenzene or ortho-trifluoromethylaniline (o-TFMA) in dichloro-methane is carried out.

o-TFMA is loaded into a reactor, fitted with a Mixel mixer, to a proportion of 79.9 kg/m³, and dichloromethane is loaded in a $CH_2Cl_2$/o-TFMA molar ratio of 31.471. Chlorine $Cl_2$ is sparged continuously into this mixture at a temperature of 20° C., to a final amount of 1.218 mol of $Cl_2$ per mole of o-TFMA.

After reaction for 60 minutes, the reaction mass takes on a pasty appearance, due to the precipitation of hydrochlorides of the amines present. This mass is then neutralized with 66.1 kg/m³ Of 30% caustic soda and then washed with water.

Analysis of the organic phase by gas chromatography gives the following results:

DC (o-TFMA)=94.0%

CY (3-chloro-2-aminotrifluoromethylbenzene)=CY (3-Cl)=0.0%

CY (5-chloro-2-aminotrifluoromethylbenzene)=CY (5-Cl)=80.7%

CY (3,5-dichloro-2-aminotrifluoromethylbenzene)=CY (3,5-diCl)=19.3%

The production of 5-chloro-2-aminotrifluoromethylbenzene is from 50 to 60 kg/m³ of reaction mixture.

The same analysis carried out on the reaction mass for lower degrees of conversion shows that the 3-chloro derivative is formed but ends up by being converted into 3,5-dichloro derivative. The results are collated in Table 1.

TABLE 1

| $Cl_2$/o-TFMA molar ratio | DC(o-TFMA) (%) | CY (3-Cl) (%) | CY (5-Cl) (%) | CY (3,5-diCl) (%) |
|---|---|---|---|---|
| 0.391 | 50.5 | 14.2 | 81.7 | 4.1 |
| 0.682 | 66.0 | 6.9 | 77.6 | 15.5 |
| 1.218 | 94.0 | 0.0 | 80.7 | 19.3 |

EXAMPLES 2 to 4—COMPARATIVE EXAMPLE 1

The same reaction is carried out by repeating the procedure of Example 1, replacing the dichloromethane with monochlorobenzene (MCB), trifluoromethylbenzene (TFMB), o-dichlorobenzene (o-DCB) and water, respectively. Table 2 below confirms that the halogenated solvents offer good selectivity, while water has a harmful effect on the selectivity of the chlorination.

TABLE 2

| Example | 1 | 2 | 3 | 4 | Comp. 1 |
|---|---|---|---|---|---|
| Solvent | $CH_2Cl_2$ | MCB | TFMB | o-DCB | Water |
| $Cl_2$/o-TFMA molar ratio | 1.218 | 1.236 | 1.322 | 1.229 | 1.129 |
| DC (o-TFMA) | 94.0 | 85.0 | 90.7 | 89.4 | 97.9 |
| CY (3-Cl) | 0.0 | 0.4 | 0.3 | 0.0 | 22.1 |
| CY (5-Cl) | 80.7 | 77.2 | 74.9 | 76.3 | 61.6 |
| CY (3,5-diCl) | 19.3 | 22.7 | 25.1 | 23.7 | 16.3 |

EXAMPLE 5

The reaction of Example 2 was reproduced at a temperature of 5° C. with a $Cl_2$/o-TFMA molar ratio of 1.780, with the following results:

DC (o-TFMA)=86.5%

CY (3-Cl)=0.6%

CY (5-Cl)=78.6%

CY (3,5-diCl)=20.7%

EXAMPLES 6 to 8

The bulk chlorination of 2-aminotrifluoro-methylbenzene (o-TFMA) is carried out.

415 g of o-TFMA are loaded into a reactor fitted with a Mixel stirrer and chlorine $Cl_2$ is sparged continuously into this mass of o-TFMA at 20° C., up to a final amount of about 0.3 mol of $Cl_2$ per mole of o-TFMA.

At the end of the reaction, the reaction mass is composed of a precipitate and an organic phase. The precipitate consisting of hydrochlorides of the various amines present is filtered off, washed with monochlorobenzene and then neutralized with caustic soda. The analyses carried out on the neutralized precipitate and on the liquid phases obtained give the following compositions:

TABLE 3

| | o-TFMA | 3-Cl | 5-Cl | 3,5-diCl |
|---|---|---|---|---|
| Precipitate (g) | 125.4 | 2.7 | 15.2 | 0.3 |
| Filtrate (g) | 126.3 | 27.9 | 73.5 | 3.3 |
| MCB washing (g) | 38.5 | 8.6 | 21.9 | 0.9 |
| Total (g) | 290.2 (1.80 mol) | 39.2 (0.200 mol) | 110.6 (0.565 mol) | 4.5 (0.020 mol) | i.e. the following molar balance:
DC (o-TFMA)=30.3%
CY (3-Cl)=25.5%
CY (5-Cl)=72.0%
CY (3,5-diCl)=2.5%

The monohalo derivatives are mainly found in the soluble part, quite probably in free base form.

Two other tests give the results collated in Table 4 below:

TABLE 4

| Example | 7 | 8 |
|---|---|---|
| Cl$_2$/o-TFMA molar ratio | 0.340 | 0.297 |
| DC (o-TFMA) | 32.0 | 26.8 |
| CY (3-Cl) | 27.5 | 26.7 |
| CY (5-Cl) | 69.3 | 71.6 |
| CY (3,5-diCl) | 3.2 | 1.6 |

In these three examples, the production efficiency of 2-amino-5-chlorotrifluoromethylbenzene is about 300 kg/m$^3$ of reaction mixture.

EXAMPLE 9

Chlorination of 2-acetamidotrifluoromethylbenzene is carried out according to the invention.

For the purposes of this example, the starting material was synthesized by acetylation of ortho-trifluoromethylaniline with acetic anhydride at 60° C., in monochlorobenzene, in a manner which is known per se, according to the equation:

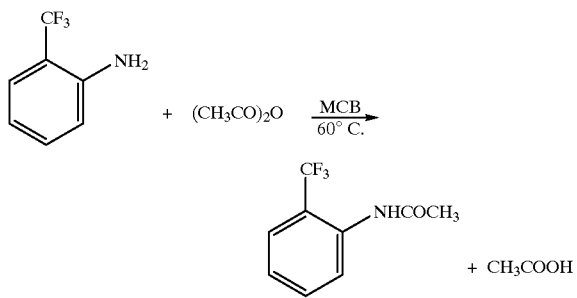

Chlorination of 2-acetamidotrifluoromethylbenzene was then carried out by reproducing the procedure of Example 2, heating to a temperature of 80° C.

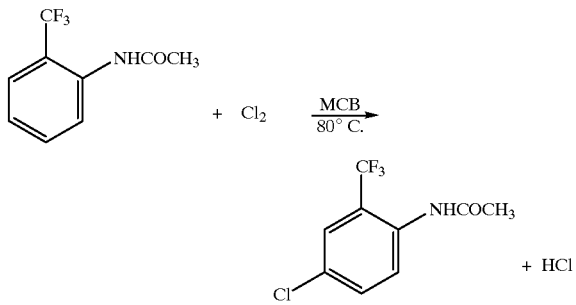

The 5-chloro-2-acetamidotrifluoromethylbenzene is formed with a CY of 66.4%.

The corresponding 5-chloro-2-aminotrifluoromethylbenzene can be isolated after methanolysis at reflux (5 hours in refluxing methanol), followed by distilling off the methyl acetate formed and the excess methanol.

EXAMPLE 10

Synthesis of 3,5-dichlorotrifluoromethylbenzene.

A-Preparation of 2-amino-3,5-dichlorotrifluoromethylbenzene

Into a mixture of 250 g of water and 250 g of monochlorobenzene, at room temperature (20 to 25° C.) are simultaneously introduced 100 g of ortho-trifluoromethylaniline at a rate of 0.54 g/min and 305 g of chlorine at a rate of 0.30 g/min (Cl$_2$/o-TFMA molar ratio= 2.111).

At the end of the reaction, the reaction mass consisting of 380 g of organic phase and 300 g of aqueous phase is neutralised with 208 g of caustic soda containing 27% by weight of NaOH (NaOH/Cl$_2$ molar ratio=1.082) and is then washed with water.

The organic phase is concentrated and distilled under vacuum (7 to 11 mbar) to isolate the 2-amino-3,5-dichlorotrifluoromethylbenzene.

The results are as follows:
DC (o-TFMA)=100.0%
CY (3-Cl)=0.2%
CY (5-Cl)=0.4%
CY (3,5-diCl)=76.6%

B-Diazotization-reduction of 2-amino-dichlorotrifluoromethylbenzene

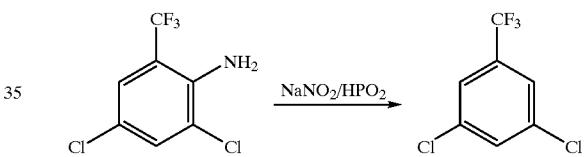

49.3 g of water, 15.8 g of 50% hypophosphorous acid (0.120 mol) and 0.13 g of copper sulfate pentahydrate (0.52·10$^{-3}$ mol) are loaded into a 500 ml reactor.

19.5 g of concentrated sulfuric acid (0.195 mol) are then added at room temperature.

23 g of 2-amino-3,5-dichlorotrifluoromethylbenzene (0.100 mol) are then added over 25 minutes at about 25° C., followed by addition of 17.1 g of 41.5% sodium nitrite solution. The temperature is maintained at a maximum of 30° C. throughout this exothermic addition, and then at 25° C. for 1 hour. The organic phase is then separated out after settling has taken place and is washed with water.

A mixture is finally obtained consisting of 22.8% aniline and 72.3% 3,5-dichlorotrifluoromethylbenzene.

The degree of conversion of the starting material was 78.2% and the true yield of dichlorotrifluoromethylbenzene is 74.0%.

It is noted that when the reaction temperature is 35° C. instead of 25° C., a mixture of 65.2% aniline and 29.6% dichlorotrifluoromethylbenzene is obtained (true yield= 28.9%; degree of conversion=40.5%).

What is claimed is:
1. A process for preparing 2-amino- or 2-acetamidotrifluoromethylbenzene derivatives halogenated in position 5 of the benzene ring, comprising a halogenation step of halogenating a compound of formula (1)

(1)

wherein Q represents an NH$_2$ group optionally in the form of an addition salt with an acid, or an NHCOCH$_3$ group, using a compound of formula X$_2$ where X represents a halogen atom, in a solvent comprising an anhydrous halogenated hydrocarbon, a mixture of water and of halogenated hydrocarbon or the compound of formula (1) itself, wherein said halogenation step does not use an organic base, to give mainly a compound of formula (2) or (3)

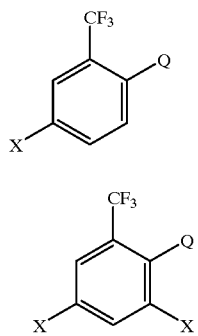

(2)

(3)

in which formulae Q and X are as defined above.

2. The process according to claim 1, wherein said solvent is an anhydrous halogenated solvent and the product mainly obtained is the compound of formula (2).

3. The process according to claim 2, wherein the molar ratio of the amount of X$_2$ introduced to the amount of compound of formula (1) is from 1 to 2.

4. The process according to claim 1, wherein the halogenation reaction is carried out until the degree of conversion of the compound of formula (1) is at least 80%.

5. The process according to claim 1, wherein said solvent comprises the compound of formula (1) itself and the product mainly obtained is the compound of formula (2).

6. The process according to claim 5, wherein the molar ratio of the amount of X$_2$ introduced to the compound of formula (1) is from 0.1 to 0.5.

7. The process according to claim 1, wherein the compound of formula (3) is mainly obtained by introducing the compound of formula (1) gradually, along with the reagent X$_2$, into a solvent comprising a mixture of halogenated hydrocarbon and water.

8. The process according to claim 7, wherein said solvent contains at least 20% by weight of halogenated hydrocarbon.

9. The process according to claim 7, wherein the molar ratio of the amount of X$_2$ introduced to the amount of compound of formula (1) introduced is from 1.5 to 2.5.

10. The process according to claim 1, wherein the temperature of the reaction medium is from 5 to 80° C.

11. The process according to claim 1, wherein Q, in formula (1), represents an NH$_2$ group optionally in the form of an addition salt, and the temperature of the reaction medium is from 5 to 50° C.

12. The process according to claim 1, wherein Q, in formula (1), represents an NHCOCH$_3$ group and the temperature of the reaction medium is from 70 to 80° C.

13. A process for preparing a dihalo derivative of 2-amino- or 2-acetamidotrifluoromethylbenzene, comprising a halogenation step of halogenating a compound of formula (2')

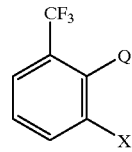

(2')

wherein Q represents as NH$_2$ group optionally in the form of an addition salt with an acid, or an NHCOCH$_3$ group, and X represents a halogen atom, using a compound of formula X$_2$ in a solvent containing a halogenated hydrocarbon, wherein said halogenation step does not use a organic base.

14. The process according to claim 1, wherein the solvent also contains water.

15. A process for preparing halo-2-aminotrifluoromethylbenzene, comprising a step of halogenating 2-acetamidotrifluoromethylbenzene

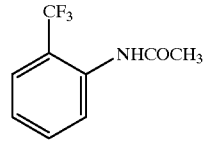

using a compound of formula X$_2$ where X represents a halogen atom, according to claim 1, to form the 5-halo-2-acetamidotrifluoromethylbenzene of formula (2)

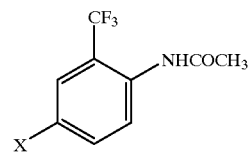

followed by a step of solvolysis of the compound of formula (2) obtained.

16. A process for preparing 3,5-dichlorotrifluoromethylbenzene, comprising a step of dihalogenating 2-aminotrifluoromethylbenzene using a compound of formula X$_2$ where X represents a halogen atom, according to a process according to claim 7, followed by a step of diazotization-reduction of the 2-amino-3,5-dihalotrifluoromethylbenzene of formula (3) obtained, in the presence of hypophosphorous acid HPO$_2$ and sodium nitrite NaNO$_2$.

17. The process according to claim 1, wherein the temperature in the diazotization-reduction step is less than or equal to 30° C.

18. A process for preparing 3,5-dichlorotrifluoromethylbenzene, comprising a step of dihalogenating 2-aminotrifluoromethylbenzene by using a compound of formula X$_2$ where X represents a halogen atom, according to a process according to claim 7, followed by a step of diazotization-reduction of the 2-amino-3,5-dihalotrifluoromethylbenzene of formula (3) obtained, in the presence of hypophosphorous acid HPO$_2$ and sodium nitrite NaNO$_2$, wherein the temperature in the diazotization-reduction step is less than or equal to 30° C.

* * * * *